United States Patent [19]
Karell

[11] Patent Number: 5,947,956
[45] Date of Patent: Sep. 7, 1999

[54] LASER APPARATUS FOR MAKING HOLES AND ETCHINGS

[76] Inventor: Manuel Leon Karell, 3573 - 22 St., San Francisco, Calif. 94114

[21] Appl. No.: 08/963,773

[22] Filed: Nov. 4, 1997

[51] Int. Cl.[6] .................................................. A61B 17/36
[52] U.S. Cl. .................................. 606/9; 607/89; 606/13
[58] Field of Search ................................ 606/2, 5, 9, 10, 606/13–15, 16–18; 607/89

[56] References Cited

U.S. PATENT DOCUMENTS

| | | |
|---|---|---|
| 4,180,058 | 12/1979 | Brem . |
| 4,525,842 | 7/1985 | Myers . |
| 4,686,979 | 8/1987 | Gruen . |
| 4,744,360 | 5/1988 | Bath . |
| 5,098,426 | 3/1992 | Sklar et al. ................................ 606/5 |
| 5,123,902 | 6/1992 | Muller . |
| 5,196,006 | 3/1993 | Klopotek et al. ......................... 606/12 |
| 5,281,141 | 1/1994 | Kowalyk . |
| 5,374,266 | 12/1994 | Kataoka . |
| 5,391,165 | 2/1995 | Fountain . |
| 5,554,153 | 9/1996 | Costello . |
| 5,743,902 | 4/1998 | Trost ........................................ 606/18 |
| 5,865,828 | 2/1999 | Jeng ........................................... 606/2 |

Primary Examiner—Linda C. M. Dvorak
Assistant Examiner—Roy Gibson

[57] ABSTRACT

The ONYCHOLASER™—a microsurgical laser unit is used to make holes in tissue, especially nails of fingers and toes. Antifungals are then topically applied to these holes for the treatment of onychomycosis. It may also be used to produce etchings of logos, phrases, pictures, scenes, cartoons etc. in nails. It may also be used for making temporary tattoos.

10 Claims, 4 Drawing Sheets

LASER APPARATUS FOR MAKING HOLES AND ETCHINGS

FIELD AND BACKGROUND OF INVENTION

The present invention, the ONYCHOLASER™, relates generally to surgical instruments and more specifically to laser microsurgical instruments for use in cutting holes or making photo decomposition (photo etchings) in tissues or membranes, especially the fingernails and toenails.

Prior to the ONYCHOLASER™—a microsurgical laser unit, when the need arose to make holes in fingernails or toenails, they were produced with a mechanical drill or with a heated wire for burning a hole. Drilling or burning of holes is standard treatment for conditions, such as traumatic subungual hematoma (blood collections under the nail after trauma).

Onychomycosis, which affects 8.4% of the population, is a persistent fungal infection of the toenails or fingernails that is unsightly and can affect a patient's quality of life. The fungus grows on the underside of the nail, causing the nail to crack, become brittle, and eventually separate from the nail bed (onycholysis). The condition is worsened in persons who have diabetes or are HIV positive, and is also worsened in many occupational pursuits involving water, moisture or chemicals.

Pharmacological treatment of onychomycosis has been less than optimal, having significant adverse reactions, such as liver or bone destruction. In many cases, a medication must be given for one year or more to be effective, with required blood sample monitoring for adverse affects. Reinfection commonly occurs on discontinuing the medication. Newer medications have shortened the treatment period, but the cost is very expensive.

U.S. Pat. No. 4,180,058 to Brem, 1979, detailed a method of treating pathological conditions of the nail in which holes were manually drilled and widened with acid. Topical antifungals were applied. This method did not gain popular professional use.

The ONYCHOLASER™—a microsurgical laser unit relates to laser devices, more particularly an apparatus and method of generating controlled multiple laser pulses to treat nail fungal infections.

The cost and reliability of laser systems have improved thereby increasing the applications for such lasers. Accurate, sealed, and permanently aligned components as in U.S. Pat. No. 4,525,842 to Myers, 1985 improved availability. Also, the concept of substances being applied to the tissue before or during the treatment, these substances being absorbent in the range of the wavelength of the laser beam for increasing absorption as in U.S. Pat. No. 5,123,902, to Muller, 1992, and as in U.S. Pat. No. 5,281,141 to Kowalyk, 1994. Surgical procedures on biological tissue may be carried out with the aid of a laser with substances being applied to the tissue before or during the treatment and these substances are absorbent in the range of the wavelength of the laser beam. Tissue removal with pulsed lasers at the eye is also the subject matter of U.S. Pat. Nos. 4,686,979 to Gruen, 1987, and 4,744,360 to Bath, 1988. U.S. Pat. No. 5,374,266 to Kataoka, 1994, provides a medical laser treatment device capable of irradiating a laser beam from the leading end of the hand piece. Also, U.S. Pat. No. 5,391,165 to Fountain, 1995, shows a laser beam delivery system whereby steering and scanning of the laser beam is accomplished in a mechanically simple and fast-responding manner. A laser skin perforator, U.S. Pat. No. 5,554,153, issued to Costello, 1996, allows blood letting.

There are several types of commercially available lasers, including argon, ruby, carbon dioxide, krypton and neodymium doped glass end YAG laser rods. YAG lasers may be preferred in certain medical applications and scientific applications because the YAG laser easily produces a short energy pulse with a high peak power.

SUMMARY OF THE INVENTION

It is an object of the ONYCHOLASER™—a microsurgical laser unit to provide a practical and satisfactory medical laser apparatus.

It is an object of the ONYCHOLASER™—a microsurgical laser unit to provide a practical and satisfactory medical laser method.

It is an object of the ONYCHOLASER™—a microsurgical laser unit to provide a practical and satisfactory nonmedical laser apparatus.

It is an object of the ONYCHOLASER™—a microsurgical laser unit to provide a practical and satisfactory nonmedical laser method.

It is a further object of the invention to provide an apparatus which improves upon the existing prior art and is especially efficient, effective, and safe.

It is a further object of the ONYCHOLASER™—a microsurgical laser unit to provide a method which improves upon the existing prior art and is especially efficient, effective, and safe.

In order to accomplish these and other objects, according to one embodiment of the ONYCHOLASER™—a microsurgical laser unit, there is provided a laser source capable of producing an output radiation beam having a predetermined wavelength. Preferably, the beam is capable of being transmitted along an optical axis, via suitable optic elements, to a hand piece or other apparatus which may be used to direct the beam to at least a portion of a nail. Holes or etching can then be produced.

It is a further object of the ONYCHOLASER™—a microsurgical laser unit to reduce fungal infection by using a substance which selectively attaches itself to the infected nail and which has certain absorptive characteristics and a laser which is chosen to have corresponding characteristics. The fungus may adsorb such substance for improving laser utility.

It is an object of the ONYCHOLASER™—a microsurgical laser unit to provide a method and apparatus for performing surgery on biological tissue, especially fingernails and toenails, by means of a laser beam, wherein its wavelength is optimally adapted to the tissue to be treated. It is a further object of the ONYCHOLASER™—a microsurgical laser unit to provide such a method and apparatus which has a good efficiency and leads to relatively small necrosis zones.

It is an object of the ONYCHOLASER™—a microsurgical laser unit to provide a method and apparatus to provide a vacuum means to remove and filter ablated particles.

It is an object of the ONYCHOLASER™—a microsurgical laser unit to provide a method and apparatus for making multiple holes or photo decomposition (photo etchings) in fingernails or toenails thus allowing for increased aeration and reduction of moistness.

It is an object of the ONYCHOLASER™—a microsurgical laser unit to provide a method to prevent the spread of fungus by placing a demarcation line of holes for aeration and moisture reduction, and applying topical fungicides or other chemicals. Thus, the spreading fungus is prevented from spreading beyond its original area of infection, and the infection is contained. Early laser treatment minimizes the chronicity of the condition, and prevents nail loss.

It is an object of the ONYCHOLASER™—a microsurgical laser unit to provide a method and apparatus which will allow for topical medications to be used more efficiently thereby obviating the need for systemic medications and the blood sample monitoring required to prevent adverse reaction of the systemic medications.

It is an object of the ONYCHOLASER™—a microsurgical laser unit to provide a method and apparatus for making holes and etchings in nails without pain, obviating need for anesthesia. A further object is to make multiple holes in an instant which is a capability of modem lasers.

It is an object of the ONYCHOLASER™—a microsurgical laser unit to provide a method and apparatus to provide a mechanism to make a specific drawing or picture on the nail for use in "nail boutiques" and "nail salons," in which a computer driven picture, scene, logo, drawing, phrase, cartoon, could be micro-etched on the nail. The etchings could then be painted or colorized for enhancing visibility.

It is an object of the ONYCHOLASER™—a microsurgical laser unit to provide a method and apparatus to provide a nail depth reader, thus directing the laser to perform the hole/etching at a certain depth, thereby preserving tissue.

It is an object of the ONYCHOLASER™—a microsurgical laser unit to provide a computer master controller means for placing holes in either grid, non-grid positions, and for photo etchings such as a logo, or trademark, or scene, or picture, or phrase, or cartoon, or tattoo. The depth of hole and etching will be determined by a measurement of nail thickness. Or the depth can be set manually. The nail depth reader means may use light, mechanical, electrical, electronic, resistive, tensile or other measurement means to ascertain the depth of the nail. Care must be taken to focus the laser in such a manner as to cut through the nail and not damage the adjacent tissue. Controlling the depth will help prevent damage to underlying tissue and pain. Also, controlling depth will help prevent secondary infections.

A memory method, such as a disk, is operatively connected to the master controller. The computer assists in making holes or etchings, for example, copying a logo and transferring it to the nails.

OPERATION

Generally, the patient or client will place his/her hand or foot, or finger or toe, into a designated cavity area of the apparatus. The physician or operator will set the controls for producing a specific desired result. For example, the operator may set the control to make holes in a grid like fashion. The nail depth reader will determine thickness of nail and compare to predetermined parameters. The laser will then automatically make the desired holes in the nail to a specified thickness. Or, had the operator set the control to etchings, the laser will then automatically make the desired etchings on the nail at a specified thickness. The computer would determine where the laser would etch, how deep to etch and the picture would give the feeling of depth as in three dimension.

It is desirable to have rapid, repetitive pulses with rapid steering and scanning of the laser beam along the target in transverse or 3D directions. The shortest time for using laser will be sought. The steering of the laser may be produced by mechanical means, such a servo motors with gears, or other means such as electronic computer means for directing where pulses occur.

If the use of the ONYCHOLASER™—a microsurgical laser unit was for the treatment of onychomycosis, then it will be repeated on all affected nails. Topical antifungals are now applied and enabled for treatment.

Or if the ONYCHOLASER™—a microsurgical laser unit was for making a photo etching, it can be repeated as needed. Also, the scenery could then be colorized by using dyes, paints or other chemicals which are absorbent or adherent; the scenery (photoetching) may have an antifungal property.

The ONYCHOLASER™—a microsurgical laser unit improves upon the prior art by providing a method and apparatus for the treatment of medical disease such as onychomycosis using a laser to produce multiple holes in an instant. These holes allow for aeration, moisture reduction and increase efficiency for topically applied antifingals. The holes may be modified into other shapes, for example, lines, squares. Other diseases may also respond to this technique.

The ONYCHOLASER™—a microsurgical laser unit improves upon the prior art by providing a method and apparatus for the making photo etchings on nails, teeth and other body parts, for example, making temporary tattoos in skin by controlling depth and preventing dyes from entering certain layers of skin.

Also, another aspect of the ONYCHOLASER™—a microsurgical laser unit is that the procedure can be carried out with the aid of substances being applied to the tissue before or during the treatment and these substances are absorbent in the range of the wavelength of the laser beam. Thus, sensitive structures are protected from the damaging effects of the laser radiation as well as from the stray radiation and fluorescence radiation triggered by the laser radiation during the application of microsurgery.

Another use for the ONYCHOLASER™—a microsurgical laser unit is the photo etching of teeth for decoration purpose, and for removing plaque.

Another use for the ONYCHOLASER™—a microsurgical laser unit is the reduction of a subungual hematoma.

Also, another object of the ONYCHOLASER™—a microsurgical laser unit is to provide a means for the laser within the position controller to be unsecured and converted to a hand held laser which could be then be used for decoration or manual positioning of holes. In addition, a hand held unit may be computer driven to provides holes and etchings, thereby reducing mechanical parts of the apparatus.

Other advantages and meritorious features of this invention will be more fully understood from the following description of the preferred embodiments and method of this invention, the appended claims, and the drawings of which brief description follows.

DESCRIPTION OF THE PREFERRED EMBODIMENTS AND METHOD

Figure 1:
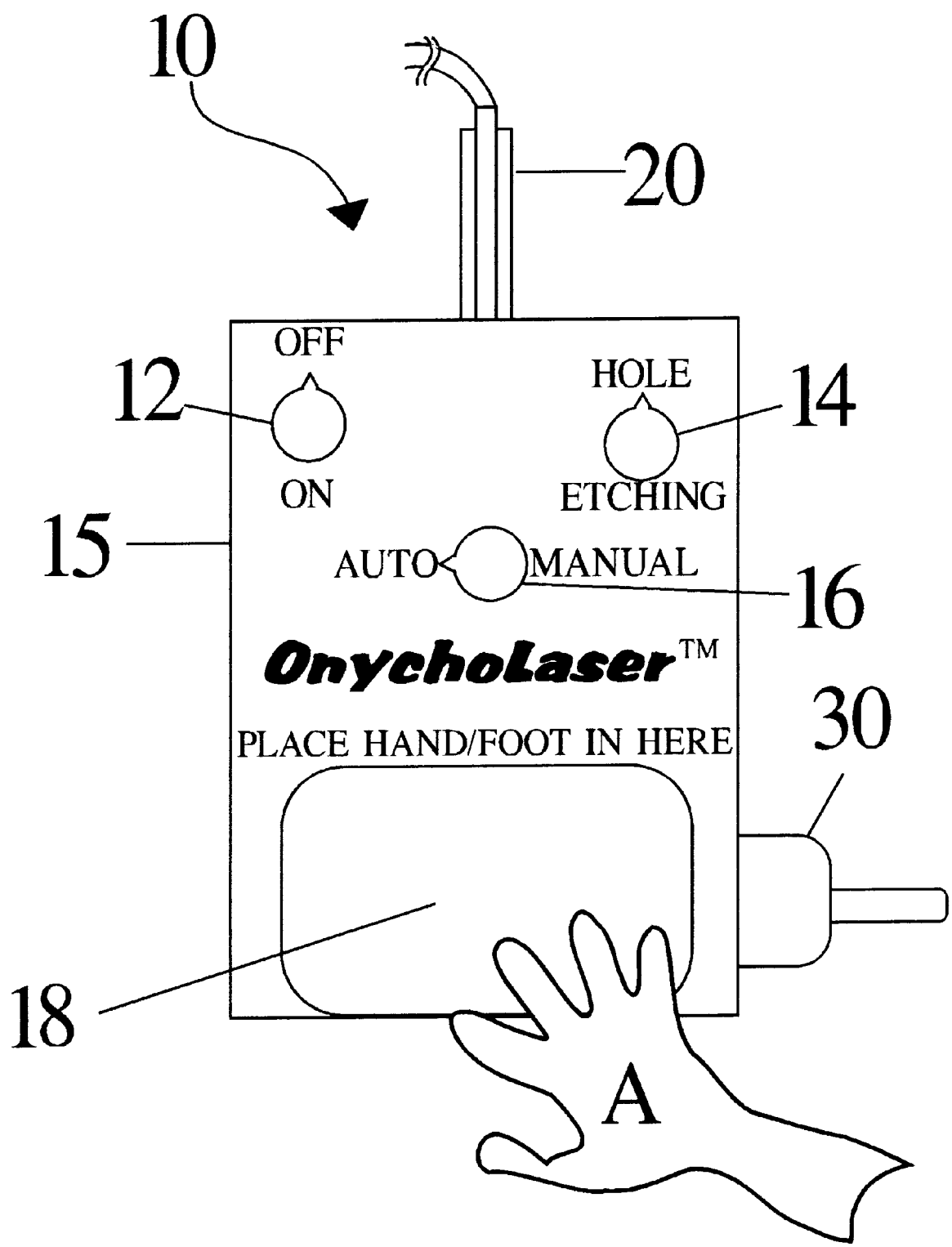
FIG. 1—shows a general schematic representation of the ONYCHOLASER™—a microsurgical laser unit, with a hand being inserted into the nail [tissue] site means FIG. 2—shows schematically the general components of the ONYCHOLASER™—a microsurgical laser unit including a laser, a nail [tissue] site means, a nail depth reader, a master controller, and a vacuum.
Figure 2:
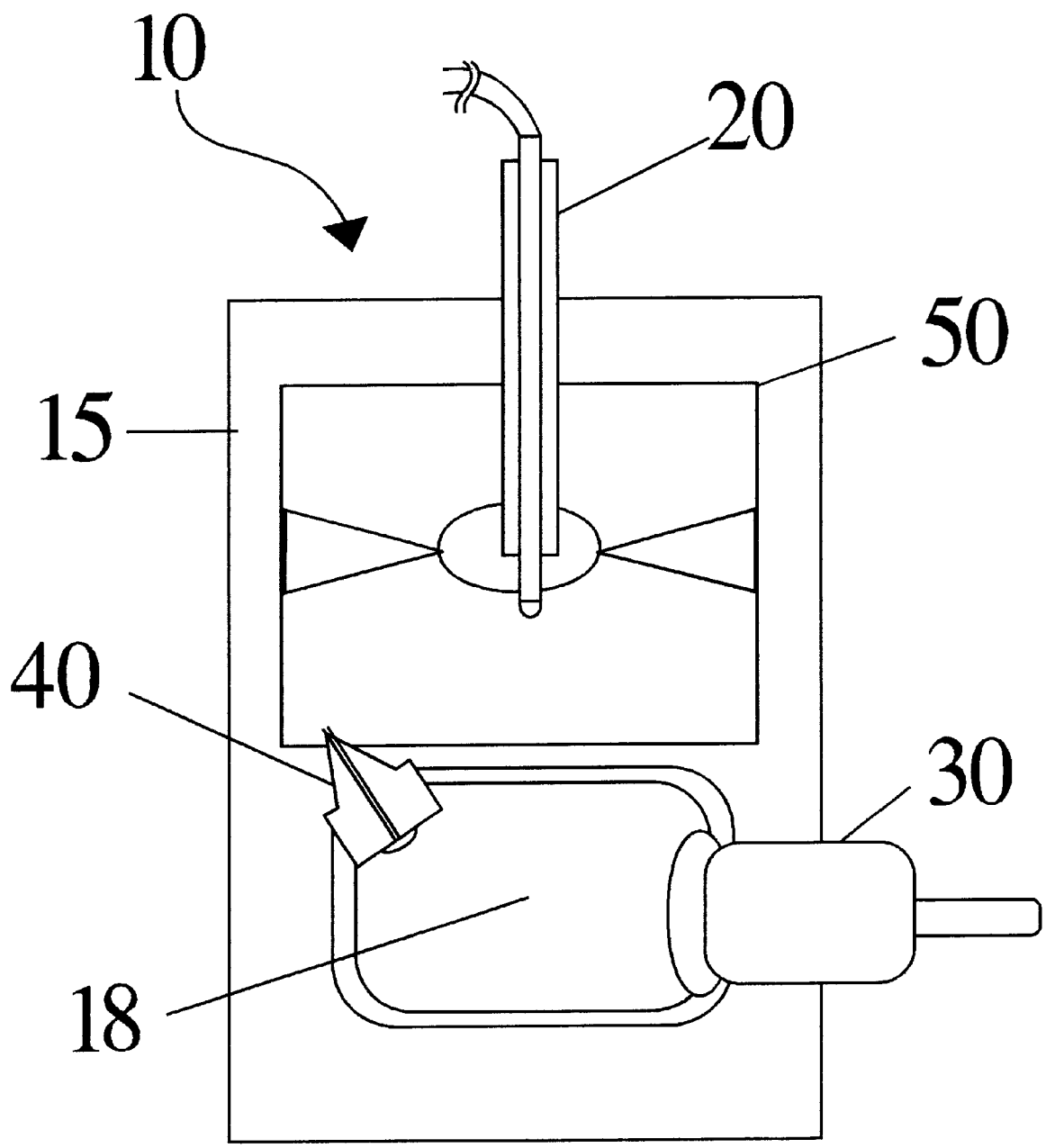
Figure 3:
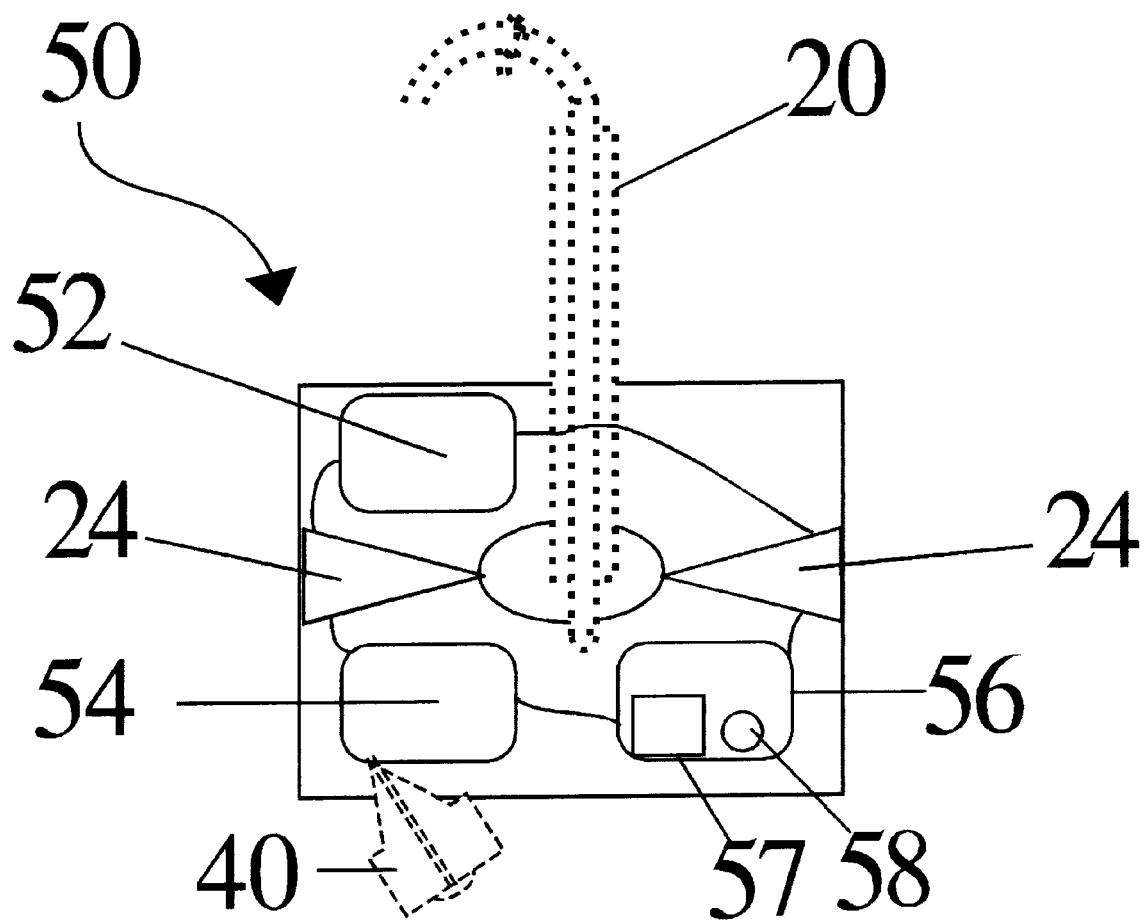
FIG. 3—shows schematically components of a master controller means having a laser moving means, a power-modifier means, and a comparer means.

Reference is now made to FIGS. 1–3 which illustrate a preferred embodiment of the ONYCHOLASER—a microsurgical laser unit. The present invention is generally numbered "10" in FIGS. 1–2. The laser apparatus(10) shown schematically in FIG. 1 is for surgery on the nail by means of laser radiation. In order to accomplish this and other objects, there is provided a laser apparatus(10) comprising a housing(15) having a laser generating source(20) and a nail [tissue] site means(18). Also depicted is an on/off means(12) for turning the apparatus on or off, a mode-switching means (14), for selecting either manual or automatic mode of operation; and a hole-etching switching means for selecting whether a hole or etching is produced. A hand(A) is being inserted into the nail [tissue] site means(18).

FIG. 2 further schematically represents this preferred embodiment in which the laser apparatus(10) additionally comprises a nail [tissue]depth sensing means(40) and a vacuum means(30) both operatively connected with said nail [tissue] site means(18). Also shown is the master controller means(50), which is seen best in FIG. 3. The master controller means(50) generally controls power output and laser movement and comprises a laser moving means(24), a power-modifier means(52), a comparer means(54), a computer means(56), a memory means(57) and a software means(58).

The general method for using this apparatus is for a hand(A) to be inserted into nail [tissue] site means(18), the on/off means(12) turned to "on" position, the hole-etching switching means(14) is turned to "hole" and the mode switching means(16) is turned to "auto". Having performed these preliminary tasks, the master controller means(50) now receives data from the nail depth sensing means(40) sends and computer means(56) which makes comparisons via a comparer means(54) and compares data to predetermined parameters. The laser generating source means(20) is activated, and holes are made into the nails. The vacuum means(30) sucks and filters out ablated material.

Figure 4:
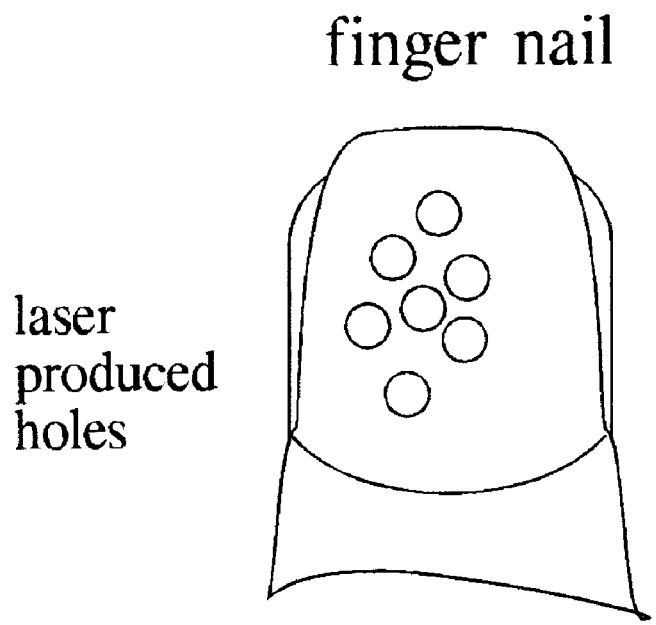
FIG. 4—shows schematically a nail with holes.

FIG. 4 shows schematically a nail with multiple punched holes. Had these holes been produced as treatment of a medical condition such as onychomycosis, then topical antifungals would have been enabled to reach and destroy the fungus.

Figure 4A:
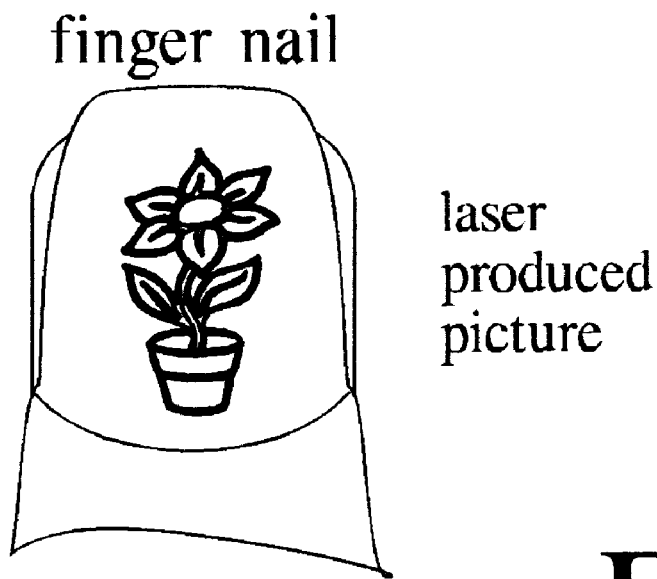
FIG. 4A—shows schematically a nail with a picture.

FIG. 4A shows schematically a picture etched into a nail.

The laser generating source(20) is capable of producing an output radiation beam having a predetermined wavelength. Preferably, the beam is capable of being transmitted along an optical axis, via suitable optic elements, to a handpiece which may then be manually used for this application.

U.S. Pat. No. 4,525,842 issued in 1985 to Myers is disclosed and is incorporated herein by reference. This patent teaches a laser device and method and provides appropriate techniques and devices amenable to the practice of the instant invention.

U.S. Pat. No. 5,554,153 issued in 1996 to Costello is disclosed and is incorporated herein by reference. This patent teaches a laser device and method and provides appropriate techniques and devices amenable to the practice of the instant invention.

The housing may be modified to fit various types and sized tissue, for example, a forearm for the purpose of producing tattoos. Thus, it is understood that the foregoing description is that of the preferred embodiment of the ONYCHOLASER™—a microsurgical laser unit and that various changes and modifications may be made thereto without departing from the spirit and scope of the invention as defined in the appended claims.

I claim:

1. A laser apparatus comprising:
   (a) a laser generating source means for producing laser light for making holes and etchings in human and animal tissue;
   (b) a tissue site means for providing a region for positioning said tissue;
   (c) said tissue site means operably conned to a tissue depth sensing means for measuring thickness of said tissue;
   (d) said laser generating source means and said tissue depth sensing means operably connected to a master controller means for controlling parameters of laser movement and power.
   (e) said laser apparatus additionally comprising a hole-etching switching means for switching between producing holes or etchings in said tissue.

2. An apparatus of claim 1 wherein said master controller means comprises:
   a laser moving means for moving laser light in all directions across said tissue; a power-modifier means for modifying power output of said laser light; a comparer means for comparing data to predetermined parameters and for producing data for laser etching of a selected image in the surface of said tissue in response to optical scanning such that peaks and valleys are created in the surface of the tissue.

3. An apparatus of claim 1 wherein said master controller means is operably connected to a computer means wherein said computer means comprises a memory means for retaining data, and software means programmable for producing a desired pattern.

4. An apparatus of claim 1 wherein said tissue site means additionally having operably attached a vacuum means for removing ablated material.

5. An apparatus of claim 1 additionally comprising a mode-switching means for switching the mode of operation between automatic or manual.

6. A laser apparatus comprising.
   (a) a laser generating source means for producing laser light for making holes and etchings in human and animal tissue;
   (b) a tissue site means for providing a region for positioning said tissue;
   (c) said tissue site means operably connected to a tissue depth sensing means for measuring thickness of said tissue;
   (d) said laser generating source means and said tissue depth sensing means operably connected to a master controller means for controlling parameters of laser movement and power wherein said master controller means additionally comprises a hole-etching switching means for switching between producing holes or etchings.

7. An apparatus of claim 6 wherein said master controller means comprises:
   a laser moving means for moving laser light in all directions across said tissue; a power-modifier means for modifying power output of said laser light; a comparer means for comparing data to predetermined parameters and for producing data for laser etching of a selected image in the surface of said tissue in response to optical scanning such that peaks and valleys are created in the surface of the tissue.

8. An apparatus of claim 6 wherein said master controller means is operably connected to a computer means wherein said computer means comprises a memory means for retaining data, and software means programmable for producing a desired pattern.

9. An apparatus of claim 6 wherein said tissue site means additionally having operably attached a vacuum means for removing ablated material.

10. An apparatus of claim 6 additionally comprising a mode-switching means for switching the mode of operation between automatic or manual.

* * * * *